(12) United States Patent
Wigbers et al.

(10) Patent No.: US 8,436,169 B2
(45) Date of Patent: May 7, 2013

(54) PROCESS FOR PREPARING 1,4-BISHYDROXYETHYLPIPERAZINE

(75) Inventors: Christof Wilhelm Wigbers, Mannheim (DE); Nina Challand, Mannheim (DE); Johann-Peter Melder, Böhl-Iggelheim (DE); Udo Rheude, Otterstadt (DE); Roman Dostalek, Neuleiningen (DE)

(73) Assignee: BASF SE (DE)

( * ) Notice: Subject to any disclaimer, the term of this patent is extended or adjusted under 35 U.S.C. 154(b) by 11 days.

(21) Appl. No.: 13/284,178

(22) Filed: Oct. 28, 2011

(65) Prior Publication Data

US 2012/0108816 A1 May 3, 2012

Related U.S. Application Data

(60) Provisional application No. 61/407,936, filed on Oct. 29, 2010.

(51) Int. Cl.
  *C07D 241/04* (2006.01)

(52) U.S. Cl.
  USPC .................. 544/398; 544/336; 544/358

(58) Field of Classification Search .................. 544/336, 544/358, 398
  See application file for complete search history.

(56) References Cited

U.S. PATENT DOCUMENTS

| | | |
|---|---|---|
| 3,166,558 A | 1/1965 | Mascioli |
| 3,997,368 A | 12/1976 | Petroff et al. |
| 4,323,550 A | 4/1982 | Goupil |
| 4,442,306 A | 4/1984 | Mueller et al. |
| 5,463,130 A | 10/1995 | Witzel et al. |
| 2008/0299390 A1 | 12/2008 | Houssin et al. |
| 2011/0218323 A1 | 9/2011 | Dahmen et al. |

FOREIGN PATENT DOCUMENTS

| | | |
|---|---|---|
| DE | 917784 C | 9/1954 |
| DE | 941909 C | 4/1956 |
| DE | 1954546 A1 | 5/1971 |
| DE | 2445303 A1 | 4/1976 |
| DE | 2628087 A1 | 1/1977 |
| DE | 2706826 A1 | 9/1977 |
| DE | 4021230 A1 | 1/1991 |
| DE | 4028295 A1 | 3/1992 |
| EP | 0070512 A1 | 1/1983 |
| EP | 0434062 A1 | 6/1991 |
| EP | 0552463 A1 | 7/1993 |
| EP | 0599180 A1 | 6/1994 |
| EP | 0673918 A1 | 9/1995 |
| GB | 1512797 A | 6/1978 |
| JP | 62145076 A | 6/1987 |
| WO | WO-92/04119 A1 | 3/1992 |
| WO | WO-2006/005505 A1 | 1/2006 |
| WO | WO-2010/054988 A2 | 5/2010 |

OTHER PUBLICATIONS

U.S. Appl. No. 13/158,667, filed Jun. 13, 2011, Wigbers et al.
International Search Report for PCT/EP2011/068700, mailed Feb. 17, 2012.
Database WPI, Week 198731, Thomson Scientific, London, GB; AN 1987-218358 (XP002664153), & JP 62 145076 A (KAO Corp) Jun. 29, 1987.

*Primary Examiner* — Golam M M Shameem
(74) *Attorney, Agent, or Firm* — Novak Druce Connolly Bove + Quigg LLP

(57) ABSTRACT

Process for preparing 1,4-bishydroxyethylpiperazine (BHEPIP) of the formula I

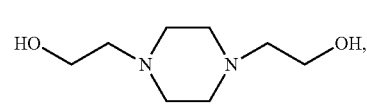

(I)

wherein diethanolamine (DEOA) of the formula II

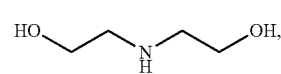

(II)

is reacted in the liquid phase in a reactor at a temperature in the range from 130 to 300° C. in the presence of a copper-comprising, chromium-free heterogeneous catalyst.

16 Claims, No Drawings

PROCESS FOR PREPARING 1,4-BISHYDROXYETHYLPIPERAZINE

CROSS-REFERENCE TO RELATED APPLICATIONS

This patent application claims the benefit of pending U.S. provisional patent application Ser. No. 61/407,936 filed Oct. 29, 2010 incorporated in its entirety herein by reference.

BACKGROUND OF THE INVENTION

The present invention relates to a process for preparing 1,4-bishydroxyethylpiperazine (BHEPIP) of the formula I

1,4-Bis(2-hydroxyethyl)piperazine I can be used for the preparation of pharmaceuticals (cf., for example, DE 2706826 A), of surfactants, as catalyst for the production of polyurethanes (cf., for example, JP 62145076 A, Kao Corp.) and as starting compound for the preparation of diazabicyclo [2.2.2]octane (DABCO) (cf., for example, U.S. Pat. No. 3,166,558 (1965), Air Products and Chem.).

1,4-Bishydroxyethylpiperazine I was prepared for the first time by reacting piperazine (PIP) with 2-chloroethanol (J. Chem. Soc. 93, page 1802 (1908)) and later also from piperazine and ethylene oxide (DE 1 954 546 A (1971), BASF AG).

Later studies showed that BHEPIP (I) can be prepared not only from piperazine but also from diethanolamine (DEOA). Diethanolamine is formed as by-product in the preparation of ethanolamine from ethylene oxide and ammonia.

Thus, BHEPIP (I) can be obtained by heating diethanolamine in the presence of monocarboxylic or dicarboxylic acids (DE 917 784 (1954), Henkel & Cie GmbH). In example 1 of DE 917 784, a mixture of diethanolamine and glacial acetic acid (molar ratio=1:0.1) was heated at 200° C. for 20 hours while stirring and passing nitrogen through the mixture and condensing water of reaction. The yield of I was 70%.

It is known from J. Am. Chem. Soc. 61, 532 (1939) that solutions of diethanolamine in dioxane can be subjected in the presence of copper chromite catalysts to a thermal treatment at from 250 to 275° C. However, the yields of BHEPIP (I) achieved under hydrogenating conditions are no higher than 50% (cf. DE 941 909 (1956), Henkel & Cie GmbH; page 2, column 1, line 26 to column 2, line 1).

The low yield of BHEPIP (I) when using copper chromite could be increased to 68% by use of catalysts comprising 48% of copper oxide, 47% of chromium oxide, 2.5% of manganese (IV) oxide and 2.5% of barium oxide (JP 62145076A, (1987), Kao Corp) (there, example 1). The catalyst was used in suspension in the presence of a solvent.

A disadvantage of the use of the copper catalysts mentioned is the toxicity of the catalyst constituent chromium. A high level of safety precautions therefore has to be undertaken in the separation, regeneration and/or disposal of these catalysts.

The earlier EP applications having the numbers 10166017.3 of Jun. 15, 2010 and 10187557.3 of Oct. 14, 2010 (both BASF SE) concern processes for preparing a cyclic tertiary amine of the formula I

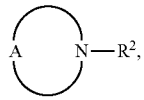

where A is a $C_4$-alkylene group, a $C_5$-alkylene group or a —$(CH_2)_2$—B—$(CH_2)_2$— group, where B is oxygen (O) or an N—$R^1$ radical and $R^1$ is $C_1$-$C_5$-alkyl, aryl or $C_5$-$C_7$-cycloalkyl, and the radical $R^2$ is methyl or linear or branched $C_2$-$C_{16}$-alkyl, $C_5$-$C_7$-cycloalkyl or $C_7$-$C_{20}$-aralkyl.

DETAILED DESCRIPTION OF THE INVENTION

It was an object of the present invention to remedy the disadvantages of the prior art and discover an improved economical process for preparing a cyclic tertiary amine. In particular, the process should make high yields, space-time yields (STY) and selectivities possible and do without the catalyst constituent chromium.

[Space-time yields are reported in "amount of product/(catalyst volume·time)" (kg/($I_{cat.}$·h)) and/or "amount of product/(reactor volume·time)" (kg/($I_{reactor}$·h)].

We have accordingly found a process for preparing 1,4-bishydroxyethylpiperazine (BHEPIP) of the formula I

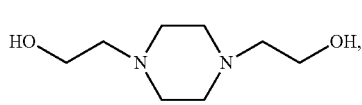

wherein diethanolamine (DEOA) of the formula II

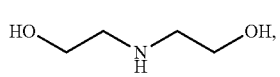

is reacted in the liquid phase in a reactor at a temperature in the range from 130 to 300° C. in the presence of a copper-comprising, chromium-free heterogeneous catalyst.

The dimerization according to the invention can be described by the following equation:

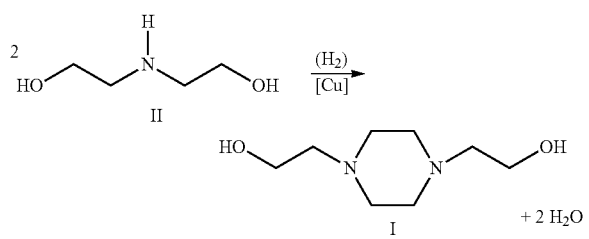

The process of the invention makes it possible to carry out the synthesis of BHEPIP (I) in one reaction step. Here, the amino alcohol II is converted with high conversions and yields into the cyclic tertiary amine I. Recirculation of incompletely alkylated or cyclized intermediates is therefore generally not necessary. However, it is possible.

The reaction temperature for the preparation of BHEPIP (I) is from 130 to 300° C., preferably from 150 to 250° C., particularly preferably from 170 to 230° C.

According to the stoichiometry of the dimerization, no hydrogen has to be introduced.

Accordingly, no hydrogen ($H_2$) is introduced into the reactor in reaction step (i) in one embodiment of the process.

However, to keep the activity of the hydrogenation catalyst constant over very long periods of time, it is advantageous to introduce hydrogen into the reaction mixture either continuously or from time to time.

The reaction pressure in the reactor is made up of the partial pressures of the starting materials and the reaction products, any solvents and introduced hydrogen at the respective reaction temperature. The pressure is increased to the desired reaction pressure by injection of hydrogen.

The total pressure (absolute) is preferably from 10 to 200 bar, preferably from 30 to 150 bar, particularly preferably from 50 to 120 bar.

If hydrogen is used, the hydrogen partial pressure is, in particular, from 0.01 to 130 bar, preferably from 0.1 to 100 bar, particularly preferably from 1 to 80 bar.

If the reaction according to the invention is carried out continuously, the space-time yield is, in particular, from 0.01 to 5 kg/($I_{cat.}$·h), preferably from 0.05 to 3 kg/($I_{cat.}$·h), particularly preferably from 0.1 to 1.0 kg/($I_{cat.}$·h). ($I_{cat.}$=catalyst bed volume).

The reaction according to the invention can be carried out without addition of a solvent.

However, it can be advantageous to use an additional solvent (which is inert under the reaction conditions). Possibilities here are, in particular, aliphatic, cycloaliphatic or aromatic solvents. Examples are n-hexane, n-octane, cyclohexane, methylcyclohexane, toluene, o-, m- or p-xylene, tetrahydrofuran, dioxane, methyl tert-butyl ether or mixtures of these compounds.

The mixture of diethanolamine (II) and solvent can comprise from 5 to 90% by weight, preferably from 10 to 80% by weight, particularly preferably from 20 to 60% by weight, of solvent.

The reaction according to the invention can be carried out batchwise or continuously. Possible reactors are, for example, stirred reactors or tube reactors. Here, the catalyst can be present in suspended form or preferably as a fixed bed. Fixed-bed reactors can be operated in the upflow mode or downflow mode.

Suitable catalysts are in principle hydrogenation catalysts, preferably copper-comprising, heterogeneous catalysts.

Many chromium-free, copper-comprising, preferably predominantly copper-comprising, catalysts which may additionally comprise at least one further element of main group I, II, III, IV or V, transition group I, II, IV, V, VII or VIII or of the lanthanides (IUPAC: groups 1 to 15 and the lanthanides), in particular Ca, Mg, Al, La, Ti, Zr, Mo, W, Mn, Ni, Co, Zn and combinations thereof are suitable in principle.

A specific embodiment of advantageous catalysts is Raney catalysts (®), especially Raney copper, and also copper-comprising metal alloys in the form of a Raney catalyst. Preference is given to Raney catalysts whose metal component comprises at least 95% by weight, in particular at least 99% by weight, of copper. Raney copper can be produced in a manner known per se by treatment of copper-aluminum alloys with alkali metal hydroxides.

A further specific embodiment of catalysts which can be particularly advantageously used are catalysts comprising copper in oxidic form and, if appropriate, additionally in elemental form.

Suitable catalysts are, for example, catalysts which comprise nickel and copper and also other metals as active constituents on a support composed of silica. Such catalysts are described, for example, in DE 26 28 087 A. The active composition of these catalyst comprises, especially, from 40 to 80% by weight of nickel, from 10 to 50% by weight of copper and from 2 to 10% by weight of manganese. EP 434 062 A describes suitable catalysts which can be obtained by reduction of a precursor composed of oxides of copper, aluminum and at least one further metal selected from among magnesium, zinc, titanium, zirconium, tin, nickel and cobalt. DE 40 21 230 A discloses copper-zirconium oxide catalysts in which the ratio of copper atoms to zirconium atoms, expressed as a weight ratio, is from 1:9 to 9:1. DE 4 028 295 A describes suitable copper-manganese hydrogenation catalysts. EP 552 463 A describes suitable catalysts whose oxidic form corresponds essentially to the composition $Cu_aAl_bZr_cMn_dO_x$, where the following relationships apply: a>0; b>0; c≧0; d>0; a>b/2; b>a/4; a>c; a>d; and x is the number of oxygen ions required to ensure electrical neutrality per formula unit. EP 552 463 A also describes suitable catalysts having a lower proportion of aluminum oxide. The catalyst according to this embodiment corresponds essentially to the composition $Cu_aAl_bZr_cMn_dO_x$, where the following relationships apply: a>0; a/40≦b≦a/4; c≧0; d>0; a>c; 0.5d≦a≦0.95d and x is the number of oxygen ions required to ensure electrical neutrality per formula unit. WO 2006/005505 A describes shaped catalyst bodies which are particularly suitable for use in the process of the invention. In a preferred embodiment, the oxidic catalyst material comprises (a) copper oxide in a proportion which obeys the relationship 50≦x≦80% by weight, preferably 55≦x≦75% by weight,
(b) aluminum oxide in a proportion which obeys the relationship 15≦y≦35% by weight, preferably 20≦y≦30% by weight, and
(c) at least one of the oxides of lanthanum, tungsten, molybdenum, titanium or zirconium, preferably of lanthanum and/or tungsten, in a proportion which obeys the relationship 2≦z≦20% by weight, preferably 3≦z≦15% by weight, in each case based on the total weight of the oxidic material after calcination, where: 80≦x+y+z≦100, in particular 95≦x+y+z≦100.

Preferred catalysts comprise the following metals in oxidic form, reduced form (elemental form) or a combination thereof. Metals which are stable in more than one oxidation state can be used entirely in one of the oxidation states or in various oxidation states:

Cu
Cu, Ti
Cu, Zr
Cu, Mn
Cu, Al
Cu, Ni, Mn
Cu, Al, at least one further metal selected from among La, W, Mo, Mn, Zn, Ti, Zr, Sn, Ni, Co
Cu, Zn, Zr
Cu, Al, Mn, optionally Zr.

As inert support material for the catalysts used according to the invention, it is possible to employ virtually all support materials of the prior art as are advantageously used in the production of supported catalysts, for example $SiO_2$ (quartz), porcelain, magnesium oxide, tin dioxide, silicon carbide, zirconium dioxide ($ZrO_2$), titanium dioxide ($TiO_2$) (rutile, anatase), $Al_2O_3$ (alumina), aluminum silicate, steatite (magnesium silicate), zirconium silicate, cerium silicate or mixtures of these support materials. Preferred support materials are aluminum oxide ($Al_2O_3$) and silicon dioxide ($SiO_2$), very particularly preferably aluminum oxide.

In a preferred embodiment of the process of the invention, copper catalysts as have been described in DE 2 445 303 A1 (BASF AG) are used. They can be considered to be amorphous products of the thermal decomposition and reduction of basic copper-aluminum carbonates and are obtained by precipitating dilute or moderately concentrated, advantageously less than 3 molar, solutions of copper and aluminum salts by means of alkali metal carbonate at pH 8-10 and decomposing the resulting precipitates at a temperature of 350-600° C. before or after appropriate shaping. Customary reduction, preferably in the presence of the alcohol used in the later reaction, gives highly active catalysts which are best suited for the present process.

An example of a suitable catalyst as disclosed in DE 24 45 303 A, obtained by heat treatment of a basic copper- and aluminum-comprising carbonate of the general composition $Cu_mAl_6(CO_3)_{0.5m}O_3(OH)_{m+12}$, where m is any, even nonintegral, number in the range from 2 to 6, is the copper-comprising precipitated catalyst disclosed in loc. cit., example 1, which is produced by treatment of a solution of copper nitrate and aluminum nitrate with sodium bicarbonate and subsequent washing, drying and heating of the precipitate.

In the suspension mode which is likewise possible in the process of the invention, the reduced copper catalyst is suspended in the reaction component diethanolamine. Suitable catalysts are, for example, Raney copper or the above-described copper catalysts in powdered form. However, preference is given to a copper-comprising material obtained by heating copper formate at 200-250° C. in the presence of an alcohol and dialkylamine. The way in which such a catalyst is formed is described, for example, in EP 70 512 A.

The catalysts can be used as shaped bodies, e.g. in the form of spheres, rings, cylinders, cubes, cuboids or other geometric bodies. Unsupported catalysts can be shaped by conventional methods, e.g. by extrusion, tableting, etc. The shape of supported catalysts is determined by the shape of the support. As an alternative, the support can be subjected to a shaping process before or after application of the catalytically active component(s). The catalysts can be used, for example, in the form of pressed cylinders, pellets, pastilles, wagon wheels, rings, stars or extrudates such as solid extrudates, polylobal extrudates, hollow extrudates and honeycomb bodies or other geometric bodies.

In the process of the invention, the catalysts are particularly preferably used in the form of catalysts which consist only of catalytically active composition and any shaping aid (e.g. graphite or stearic acid) if the catalyst is used as shaping body, i.e. do not comprise any further catalytically active accompanying materials.

In this context, oxidic support material (particularly preferably aluminum oxide ($Al_2O_3$)) is considered as part of the catalytically active composition.

The catalysts are preferably used by arranging the catalytically active composition after milling, mixing with shaping aids, shaping and heat treatment as shaped catalyst bodies, e.g. as pellets, spheres, rings, extrudates (e.g. rods), in the reactor.

The indicated concentrations (in % by weight) of the components of the catalyst are in each case based, unless indicated otherwise, on the catalytically active composition of the finished catalyst after its last heat treatment and before reduction with hydrogen.

The catalytically active composition of the catalyst after its last heat treatment and before reduction with hydrogen is defined as the sum of the masses of the catalytically active constituents and the abovementioned catalyst support material and preferably comprises essentially the following constituents:

aluminum oxide ($Al_2O_3$) and oxygen-comprising compounds of copper and preferably oxygen-comprising compounds of sodium.

The sum of the abovementioned constituents of the catalytically active composition, calculated as $Al_2O_3$, CuO and $Na_2O$, is usually from 70 to 100% by weight, preferably from 80 to 100% by weight, particularly preferably from 90 to 100% by weight, more preferably from 98 to 100% by weight, more preferably $\geq$99% by weight, very particularly preferably 100% by weight.

The catalytically active composition of the catalysts used in the process of the invention can further comprise one or more elements (oxidation state 0) or inorganic or organic compounds thereof selected from groups I A to VI A and I B to VII B and VIII of the Periodic Table.

Examples of such elements and compounds thereof are: transition metals such as Ni and NiO, Co and CoO, Re and rhenium oxides, Mn and $MnO_2$, Mo and molybdenum oxides, W and tungsten oxides, Ta and tantalum oxides, Nb and niobium oxides or niobium oxalate, V and vanadium oxides and vanadyl pyrophosphate; lanthanides such as Ce and $CeO_2$ or Pr and $Pr_2O_3$; alkali metal oxides such as $K_2O$; alkali metal carbonates such as $Na_2CO_3$; alkaline earth metal oxides such as CaO, SrO; alkaline earth metal carbonates such as $MgCO_3$, $CaCO_3$ and $BaCO_3$; boron oxide ($B_2O_3$).

The catalytically active composition of the catalysts used in the process of the invention after its last heat treatment and before reduction with hydrogen comprises, in particular, from 20 to 80% by weight, preferably from 30 to 70% by weight, particularly preferably from 35 to 60% by weight, of aluminum oxide ($Al_2O_3$) and from 20 to 80% by weight, preferably from 30 to 70% by weight, particularly preferably from 40 to 65% by weight, very particularly preferably from 45 to 60% by weight, of oxygen-comprising compounds of copper, calculated as CuO, from 0 to 2% by weight, preferably from 0.05 to 1% by weight, particularly preferably from 0.1 to 0.5% by weight, of oxygen-comprising compounds of sodium, calculated as $Na_2O$, less than 5% by weight, e.g. from 0.1 to 4% by weight, preferably less than 1% by weight, e.g. from 0 to 0.8% by weight, of oxygen-comprising compounds of nickel, calculated as NiO.

The catalytically active composition of the catalyst before reduction with hydrogen particularly preferably comprises less than 1% by weight, e.g. from 0 to 0.5% by weight, of oxygen-comprising compounds of cobalt, calculated as CoO.

The catalytically active composition of the catalyst used in the process of the invention very particularly preferably comprises no nickel, no cobalt and/or no ruthenium, in each case neither in metallic form (oxidation state 0) nor in an ionic, in particular oxidized, form.

The oxygen-comprising compounds of copper are, in particular, copper(I) oxide and copper(II) oxide, preferably copper(II) oxide.

The catalytically active composition of the catalyst used in the process of the invention very particularly preferably does not contain any zirconium dioxide ($ZrO_2$), titanium dioxide ($TiO_2$) and/or silicon dioxide ($SiO_2$).

In a particularly preferred embodiment, the catalytically active composition of the catalysts used in the process of the invention does not comprise any further catalytically active component, either in elemental form or in ionic form.

In a particularly preferred embodiment, the catalytically active composition is not doped with further metals or metal compounds.

However, usual accompanying trace elements originating from isolation of the metals Cu and, if appropriate, Ni are preferably excluded from this.

Various processes are possible for producing the catalysts used in the process of the invention. They can be obtained, for example, by peptizing pulverulent mixtures of the hydroxides, carbonates, oxides and/or other salts of the components aluminum, copper, optionally sodium by means of water and subsequently extruding and heat treating the composition obtained in this way.

The catalysts which are preferably used in the process of the invention can also be produced by impregnation of aluminum oxide ($Al_2O_3$) which is, for example, present in the form of powder or pellets.

Aluminum oxide can be used in various modifications, with preference being given to α—(alpha), γ—(gamma) or θ-$Al_2O_3$ (theta-$Al_2O_3$). Particular preference is given to using γ-$Al_2O_3$.

The shaped bodies of aluminum oxide can be produced by conventional methods.

The impregnation of the aluminum oxide is likewise carried out by conventional methods, as described, for example, in EP 599 180 A, EP 673 918 A or A. B. Stiles, Catalyst Manufacture—Laboratory and Commercial Preparations, Marcel Dekker, New York (1983), by application of an appropriate metal salt solution in one or more impregnation stages using, for example, appropriate nitrates, acetates or chlorides as metal salts. The composition is dried and if appropriate calcined after impregnation.

Impregnation can also be carried out by the "incipient wetness" method in which the inorganic oxide (i.e. aluminum oxide) is moistened with the impregnation solution in accordance with its water absorption capacity to not more than saturation. However, impregnation can also be carried out in supernatant solution.

In the case of multistage impregnation processes, it is advantageous to dry and if appropriate calcine the support between individual impregnation steps. Multistage impregnation is particularly advantageous when a relatively large amount of metal is to be applied to the inorganic oxide.

To apply a plurality of metal components to the inorganic oxide, the impregnation can be carried out using all metal salts simultaneously or using the individual metal salts in succession in any order.

Precipitation methods are preferably employed for producing the catalysts which are preferably used in the process of the invention. Thus, they can be obtained, for example, by coprecipitation of the components from an aqueous salt solution by means of mineral bases in the presence of a slurry of a sparingly soluble, oxygen-comprising aluminum compound and subsequent washing, drying and calcination of the precipitate obtained. As sparingly soluble, oxygen-comprising aluminum compound, it is possible to use, for example, aluminum oxide. The slurries of the sparingly soluble aluminum compound can be produced by suspending finely particulate powders of this compound in water with vigorous stirring. These slurries are advantageously obtained by precipitation of the sparingly soluble aluminum compound from aqueous aluminum salt solutions by means of mineral bases.

The catalysts which are preferably used in the process of the invention are preferably produced by coprecipitation (mixed precipitation) of all their components. For this purpose, an aqueous salt solution comprising the catalyst components is advantageously admixed, hot and while stirring, with an aqueous mineral base, in particular an alkali metal base, for example sodium carbonate, sodium hydroxide, potassium carbonate or potassium hydroxide, until precipitation is complete. The type of salts used is generally not critical: since the water-solubility of the salts is of primary importance in this procedure, a criterion is for the salts to have the good water-solubility required for producing these comparatively highly concentrated salt solutions. It is considered to be self evident that when choosing the salts of the individual components, naturally only salts having anions which do not lead to interference, whether by causing undesirable precipitations or by making the precipitation difficult or impossible by complex formation, will be selected.

The precipitates obtained in these precipitation reactions are generally chemically nonuniform and comprise, inter alia, mixtures of the oxides, oxide hydrates, hydroxides, carbonates and insoluble and basic salts of the metal or metals used. It can be advantageous in terms of the filterability of the precipitates for them to be aged, i.e. for them to be left to stand for some time after the precipitation, if appropriate hot or with air being passed through.

The precipitates obtained by these precipitation processes are processed further in a conventional way to form the catalysts used according to the invention. After washing, they are preferably dried at from 80 to 200° C., preferably from 100 to 150° C., and then calcined. Calcination is preferably carried out at temperatures in the range from 300 to 800° C., preferably from 400 to 600° C., in particular from 450 to 550° C.

After calcination, the catalyst is advantageously conditioned, either by bringing it to a particular particle size by milling and/or by mixing it with shaping aids such as graphite or stearic acid after milling, pressing it by means of a press to form shaped bodies, namely pellets, and heat treating it. The heat treatment temperatures preferably correspond to the temperatures in the calcination.

The catalysts produced in this way comprise the catalytically active metals in the form of a mixture of oxygen-comprising compounds thereof, i.e. in particular as oxides and mixed oxides.

The catalysts produced in this way can be stored as such. Before use as catalysts, they are usually prereduced. However, they can also be used without prereduction, in which case they are then reduced by the hydrogen present in the reactor under the conditions of the hydrogenative amination.

To carry out the prereduction, the catalysts are initially exposed to a nitrogen-hydrogen atmosphere at preferably from 150 to 200° C. for a period of, for example, from 12 to 20 hours and subsequently treated in a hydrogen atmosphere at preferably from 200 to 400° C. for up to about 24 hours. In this prereduction, part of the oxygen-comprising metal compound(s) present in the catalysts is/are reduced to the corresponding metal(s), so that the latter are present together with the various oxygen compounds in the active form of the catalyst.

The reaction in the process of the invention is preferably carried out in a tube reactor.

In a single train plant, the tube reactor in which the preferably isothermal reaction is carried out comprises a series arrangement of a plurality of (e.g., two or three) individual tube reactors.

The preferably isothermal reaction in the process of the invention is preferably carried out with a temperature deviation of not more than +/−8° C., particularly preferably not more than +/−5° C., in particular not more than +/−4° C., very particularly preferably not more than +/−3° C., e.g. from +/−0 to not more than +/−2° C. or from +/−0 to not more than +/−1° C.

These temperature deviations are based on the respective temperatures in the respective catalyst bed, at the point of entry of the starting materials into the catalyst bed and the point of exit of the reaction mixture from the catalyst bed.

It is possible for a plurality of catalyst beds to be connected or arranged in parallel or in series.

If a plurality of catalyst beds are connected in series, the abovementioned temperature deviations in the isothermal mode of operation which is preferred according to the invention relate to the respective temperature in the catalyst bed, at the point of entry of the starting materials into the first catalyst bed and the point of exit of the reaction mixture from the last catalyst bed.

In a preferred embodiment, the reactor tube is heated from the outside by means of a stream of heat transfer medium, with the heat transfer medium being able to be, for example, an oil, a salt melt or another heat-transferring liquid.

The process of the invention is preferably carried out continuously, with the catalyst preferably being arranged as a fixed bed in the reactor. Flow into the fixed catalyst bed can be either from the top or from the bottom.

The water of reaction formed in the course of the reaction generally does not have any adverse effect on the conversion, the reaction rate, the selectivity and the operating life of the catalyst and is therefore advantageously removed from the reaction product only during the work-up of the latter, e.g. by distillation.

A further preferred embodiment comprises removing the water of reaction by azeotropic distillation using a solvent which forms a heteroazeotrope with water (e.g. benzene, toluene, xylene). The distillate from the azeotropic distillation forms a two-phase liquid mixture after cooling and depressurization. After phase separation, water is discharged and the organic phase (i.e. the solvent) is recirculated to the work-up step.

The liquid reaction output obtained after cooling and depressurization is optionally separated off from the suspended catalyst. The catalyst-free reaction output may comprise unreacted diethanolamine II and water formed in addition to the target product, viz. the tertiary amine I. Two mol of water are formed per mole of diethanolamine used.

The reaction output can be worked up by distillation. Here, water of reaction, if appropriate solvent and any unreacted diethanolamine II are firstly separated off at the top. The bottom product comprising predominantly BHEPIP (I) can be purified by further fractional distillation. Unreacted diethanolamine II can be recirculated to the synthesis stage.

1,4-Bishydroxyethylpiperazine I has a melting point of 135° C. It is therefore also possible to separate off I in crystalline form, e.g. by filtration or centrifugation.

The dimerization of diethanolamine II can occur via the intermediate III:

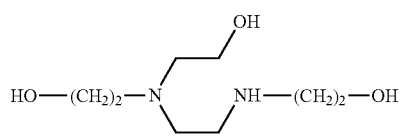

(III)

All pressures indicated are absolute pressures.

EXAMPLES

The following examples were carried out using a copper catalyst having the composition 55% by weight of CuO and 45% by weight of gamma-$Al_2O_3$ (after its last heat treatment and before reduction with hydrogen) (catalyst A).

The catalyst was produced by impregnation of gamma-$Al_2O_3$ powder with an aqueous copper nitrate solution. Tableting was carried out by the conventional methods. Before commencement of the reaction, the catalyst was reduced in a stream of hydrogen at about 200° C. (see below). The reported yields of BHEPIP (I) are % by area values determined by gas chromatography.

Example 1

Preparation of 1,4-bis(hydroxyethyl)piperazine I from diethanolamine (solvent: tetrahydrofuran)

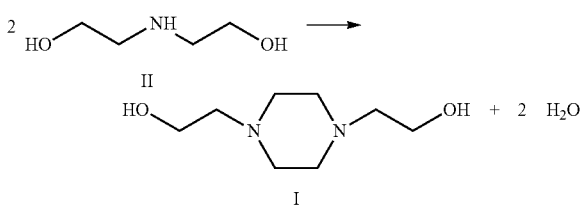

The reaction was carried out in a magnetically coupled 300 ml stirring autoclave with electric heating and cascade regulation of the internal temperature.

31.5 g of diethanolamine (II) (0.3 mol), 50 g of tetrahydrofuran (THF) and 10 g of the reduced and passivated, copper-on-aluminum oxide catalyst A (3×3 mm pellets) were introduced into the autoclave which had been made inert by means of nitrogen. Before reduction, the catalyst comprised 55% by weight of copper oxide (CuO) and 45% by weight of aluminum oxide. The reduction was carried out at 180 to 200° C. before the reaction, and the passivation was carried out at <50° C. using air. The reaction mixture was pressurized at room temperature with hydrogen up to a pressure of 10 bar. The reaction mixture was then heated to 200° C., further hydrogen was injected to a total pressure of 80 bar and the mixture was stirred at 200° C. and 80 bar (700 rpm) for 10 hours.

Gas-chromatographic analysis (GC column: 30 m RTX 5 Amin) indicated that the reaction output comprised, at quantitative diethanolamine conversion, 73% of 1,4-bis(hydroxyethyl)-piperazine (not including THF).

Example 2

Preparation of 1,4-bis(hydroxyethyl)piperazine from diethanolamine (no solvent)

Example 2 was carried out under the conditions of example 1 in the same apparatus. 100 g of diethanolamine (II) and 10 g of catalyst A were used. Gas chromatographic analysis (GC column: 30 m RTX Amin) indicated, at quantitative diethanolamine conversion, that the reaction output comprised 79% of 1,4-bis(hydroxyethyl)piperazine.

The example shows that, according to the invention, 1,4-bis(hydroxyethyl)piperazine I can also be prepared in high yield without use of a solvent, here in a fixed-bed mode of operation.

The invention claimed is:
1. A process for preparing 1,4-bishydroxyethylpiperazine (BHEPIP) of the formula I

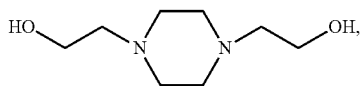

comprising reacting diethanolamine (DEOA) of the formula II

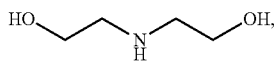

in the liquid phase in a reactor at a temperature in the range of from 130 to 300° C. in the presence of a copper-comprising, chromium-free heterogeneous catalyst, wherein said catalyst comprises a catalytically active composition before reduction with hydrogen.

2. The process according to claim 1, wherein the catalyst comprises copper and aluminum oxide.

3. The process according to claim 1, wherein the catalytically active composition of the catalyst before reduction with hydrogen comprises
from 20 to 80% by weight of aluminum oxide,
from 20 to 80% by weight of oxygen-comprising compounds of copper, calculated as CuO,
from 0 to 2% by weight of oxygen-comprising compounds of sodium, calculated as $Na_2O$, and
less than 5% by weight of oxygen-comprising compounds of nickel, calculated as NiO.

4. The process according to claim 1, wherein the catalytically active composition of the catalyst before reduction with hydrogen comprises less than 1% by weight of oxygen-comprising compounds of nickel, calculated as NiO.

5. The process according to claim 1, wherein the catalytically active composition of the catalyst before reduction with hydrogen comprises less than 1% by weight of oxygen-comprising compounds of cobalt, calculated as CoO.

6. The process according to claim 1, wherein the catalytically active composition of the catalyst before reduction with hydrogen comprises
from 30 to 70% by weight of aluminum oxide and
from 30 to 70% by weight of oxygen-comprising compounds of copper, calculated as CuO.

7. The process according to claim 1, wherein the catalytically active composition of the catalyst before reduction with hydrogen comprises from 0.05 to 1% by weight of oxygen-comprising compounds of sodium, calculated as $Na_2O$.

8. The process according to claim 1, wherein the catalytically active composition of the catalyst does not comprise any nickel, cobalt, or ruthenium.

9. The process according to claim 1, wherein the reaction is carried out isothermally with a temperature deviation of not more than +/−8° C.

10. The process according to claim 1, wherein the reaction is carried out in the presence of hydrogen ($H_2$).

11. The process according to claim 1, wherein the reaction is carried out continuously.

12. The process according to claim 11, wherein the reaction is carried out in a tube reactor.

13. The process according to claim 11, wherein the reaction is carried out in a shell-and-tube reactor or in a single-train plant.

14. The process according to claim 1, wherein the reaction is carried out at an absolute pressure in the range of from 10 to 200 bar.

15. The process according to claim 1, wherein the catalyst is arranged as a fixed bed in the reactor.

16. The process according to claim 1, wherein the reaction is carried out in the absence of a solvent.

* * * * *